United States Patent [19]  [11] Patent Number: 4,735,799
Patarroyo  [45] Date of Patent: Apr. 5, 1988

[54] MALARIA VACCINE

[76] Inventor: Manuel E. Patarroyo, P.O. Box 4402, Bogota, Colombia

[21] Appl. No.: 3,194

[22] Filed: Jan. 14, 1987

[51] Int. Cl.⁴ ............... A61K 39/00; C07K 7/06; C07K 7/08
[52] U.S. Cl. ................................. 424/88; 530/327
[58] Field of Search .......................... 424/88; 530/327

[56] References Cited
PUBLICATIONS
Nature 311 (1984) 382–385.

Primary Examiner—Delbert R. Phillips
Attorney, Agent, or Firm—Abelman Frayne Rezac & Schwab

[57] ABSTRACT

A mixture of the synthetic peptide compounds of the formulas:

Try-Gly-Gly-Pro-Ala-Asn-Lys-Lys-Asn-Ala-Gly-OH,    Formula (I)

Asp-Glu-Leu-Glu-Ala-Glu-Thr-Gln-Asn-Val-Tyr-Ala-Ala-NH₂,    Formula (II)

and

Tyr-Ser-Leu-Phe-Gln-Lys-Glu-Lys-Met-Val-Leu-NH₂,    Formula (III)

and compositions thereof, induces antibodies against the late stages of *Plasmodium falciparum* malaria and provides protection against infection with this parasite, thus providing a synthetic malaria vaccine for *Plasmodium falciparum* induced malaria.

19 Claims, No Drawings

MALARIA VACCINE

BACKGROUND OF THE INVENTION

This invention relates generally to the chemical synthesis of certain peptides and, more particularly, to the use of a mixture of certain of these synthesized peptides as a synthetic vaccine against malaria.

To eradicate malaria, which is dangerously spreading in the developing countries, where more than half of the world's susceptible population lives, scientists are looking for means to control, via chemically synthesized or genetically engineered vaccines, this deadly and threatening parasitic disease.

There are four species of human plasmodia parasites: *Plasmodium vivax; P. ovale; P. malariae* and *P. falciparum. P. falciparum* is the most common and lethal. When the malaria infected anopheles mosquito, bites a non-immune person it injects infectious forms of the parasite called sporozoites (first stage) living inside her salivary glands, into the host bloodstream, which within 5 minutes reaches the liver, infecting the liver cells and remains there for about one week.

Each one of these infectious particles or sporozoites divides into 20,000 to 30,000 merozoites (second stage) contained in a bag, or schizont, inside the liver cells. When the cells burst, the merozoites enter the bloodstream and invade circulating red blood cells. Inside these red blood cells (or asexual blood stage), merozoites grow, evolving through several and successive differentiation stages, namely, ring, trophozoite, schizont and merozoite, dividing and breaking out every 48 hours and producing the clinical symptoms of the disease, such as chills and fever, typical of the major forms of malaria. Each new merozoite produces 16-32 offspring that in turn infect new red blood cells, perpetuating the disease and its clinical symptoms.

After several weeks some merozoites differentiate into either male or female gametocytes (third or sexual blood stage) in the bloodstream and when another mosquito bites, it sucks up the malaria infected red blood cells containing gametocytes. Inside the female mosquito the gametocytes break out of the cells and fuse, forming a new generation of sporozoites starting the cycle once again.

A conventional vaccine using attenuated or dead malaria parasites is not feasible due to difficulties in obtaining large amounts of merozoites and containing red blood cell debris which potentially will create an autoimmune hemolytic anemia. In fact it was not until 1976 when William Trager developed a laboratory method to enable one to grow small amounts of *P. falciparum* blood in asexual stages (British Medical Bulletin 38:129, 1982).

The alternatives are then the development by modern techniques, such as chemical synthesis or recombinant DNA, of proteins able to induce protective immunity against the parasite infection.

In this regard, several groups have tried to identify potential targets for immunological attack of the extracellular stages of the parasite, namely, sporozoite, merozoite and gametocytes, the first two being briefly exposed in the blood circulation to the immune system.

Nussenzweig et al. (J. Exp. Med. 156:20, 1982) have identified a protein localized on the surface of sporozoites. Antibodies against this structure confer protection against the experimental disease. It is, however, generally accepted that a vaccine based only on sporozoites will not suffice to prevent malaria. Research to develop a polyvalent vaccine including merozoite and sporozoites targets is actively being pursued in many laboratories throughout the world.

Freeman and Holder (J. Exp. Med. 158:1647, 1983) have characterized a major antigen on the surface of merozoites of 195KD (kilodaltons) protein that generates, upon cleavage, protions of 83KD, 42KD and 19KD. The first of these, the 83KD protein, remains on the surface of the merozoites. The data suggests that this antigen could be a possible target of protective immunity. Separately, Perrin et al. (J. Exp. Med. 160:441, 1984) have shown protection against blood stage induced malaria in squirrel monkeys when vaccinated with a protein of 140KD.

Perlmann et al. (J. Exp. Med. 159:1686, 1984) have recognized that 155KD protein antigen is invariably deposited on the surface of the *P. falciparum* infected red blood cells and clinical immunity in endemic areas appears to correlate with antibodies raised against certain parts of this molecule. Collins et al. (Nature 323:259, Sept. 18, 1986) have shown partial protection of *Aotus trivirgatus* monkeys immunized with genetically engineered fragments of this 155KD protein.

SUMMARY OF THE INVENTION

It has been found that a mixture of the following chemically synthesized novel peptide compounds, having the formulas:

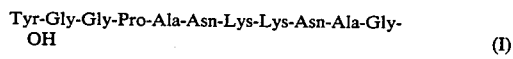

Tyr-Gly-Gly-Pro-Ala-Asn-Lys-Lys-Asn-Ala-Gly-OH     (I)

and

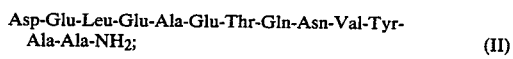

Asp-Glu-Leu-Glu-Ala-Glu-Thr-Gln-Asn-Val-Tyr-Ala-Ala-NH₂;     (II)

and a chemically synthesized, novel peptide compound selected from the group consisting of:

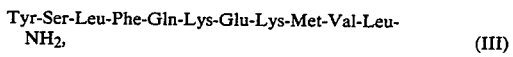

Tyr-Ser-Leu-Phe-Gln-Lys-Glu-Lys-Met-Val-Leu-NH₂,     (III)

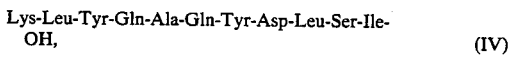

Lys-Leu-Tyr-Gln-Ala-Gln-Tyr-Asp-Leu-Ser-Ile-OH,     (IV)

or

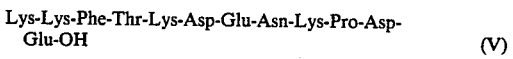

Lys-Lys-Phe-Thr-Lys-Asp-Glu-Asn-Lys-Pro-Asp-Glu-OH     (V)

provide complete protective immunity against *P. falciparum* malaria.

When an equal mixture, weight-by-weight, of the peptide compounds of Formulas I, II and III, were injected in the form of a vaccine into the highly susceptible experimental model, the *Aotus trivirgatus* monkey, high antibody titers were induced against the peptides themselves and also reacted with the *Plasmodium falciparum* parasite by different immunological methods. The mixture of peptides of Formulas I, II and III were able to induce protective immunity in the immunized monkeys since animals vaccinated with this mixture of peptides either did not develop the disease, or else developed a mild parasitemia when injected with the lethal live, fresh *Plasmodium falciparum* parasites.

DETAILED DESCRIPTION OF THE INVENTION

It has been established that a mixture of the following novel peptide compounds represents a preferred embodiment of the present invention, namely, Tyr-Gly-Gly-Pro-Ala-Asn-Lys-Lys-Asn-Ala-Gly-OH,  Formula (I)

Asp-Glu-Leu-Glu-Ala-Glu-Thr-Gln-Asn-Val-Tyr-Ala-Ala-$NH_2$,  Formula (II)

and

Tyr-Ser-Leu-Phe-Gln-Lys-Glu-Lys-Met-Val-Leu-$NH_2$,  Formula (III)

when employed in about a 1:1:1 mixture, weight-by-weight, up to about a 10:10:10 mixture, weight-by-weight, provide a synthetic vaccine which has been found to provide complete protective immunity against *P. falciparum* induced malaria.

The novel peptide compounds of the present invention and their properties as a vaccine for *P. falciparum* malaria when employed in a mixture were determined in the following fashion.

As a result of my investigations, protein molecules of 155KD, 83KD, 55KD and 35KD, which are specific for the late schizont and merozoite stages of the *P. falciparum* parasite, were found capable of eliciting either partial or total protective immunity in Aotus monkeys immunized with the individual proteins and experimentally infected with *P. falciparum* parasites.

The synthesized peptide compounds of Formulas I and II are alpha hydrophilic structures, corresponding to the amino terminal parts of the molecules 35KD and 55KD, respectively, which offer in some vaccinated animals protective immunity against *P. falciparum* malaria in a fashion similar to the naturally occuring protein in the merozoite parasite. Each of the peptide compounds represented by Formulas I and II, even when they were employed individually, elicited antibodies and as a result delayed in some vaccinated animals the appearance of parasitemia for a period of two to five days when compared with non-immunized controls, or animals immunized with other peptide compounds.

When the peptide compounds of Formulas I and II were employed as a 1:1 mixture, weight-by-weight, 50% of the immunized animals developed mild parasitemia from which they spontaneously recovered, while the other 50% were not protected at all, suggesting that this particular mixture of peptide compounds provides partial protective immunity against *P. falciparum* induced malaria, rather than complete protective immunity.

The novel peptide compounds according to Formula III, IV and V were synthesized according to a specific amino acid sequence of the 195KD protein described by Holder et al. in Nature, Vol. 317, pages 270–273, September 1985. Of the fifteen (15) peptides which were synthesized, most of them induced antibodies, but only the three peptides compounds, according to Formulas III, IV and V, provided partial protective immunity against *P. falciparum* induced malaria.

The peptide of Formula III, which corresponds to amino acid residues 43–53 of the 195KD amino acid sequence, has an alpha hydrophilic structure. The peptide of Formula IV, which corresponds to residues 277–287 of the 195KD amino acid sequence, has a random structure, while the peptide of Formula V, corresponding to residues 595–606 of the 195KD amino acid sequence, has a reverse turn structure according to the Chou Fassman method of determining the secondary structure. (Adv. Enzymol. 47:45, 1978)

The individual peptide compounds of Formulas III and V each induced a delay in the appearance of parasitemia in some animals when used for immunization against the *P. falciparum* induced malaria. The peptide compound of Formula IV when used individually for immunization, induced a spontaneous recovery in two of the four vaccinated animals against the *P. falciparum* induced malaria.

The peptide compounds of the present invention can be coupled to a carrier molecule, e.g., bovine serum albumin, by glutaraldehyde or any other coupling agent in order to induce a better immune response against the peptide due to the increased size of the molecule. Another available means for inducing a better immune response would be to copolymerize a mixture of two or three of the peptide compounds of the present invention to increase the size of the molecule.

Since the peptide compounds of the present invention are hydrophilic in nature, any mixture of the peptides can readily be prepared into an injectable form of the vaccine for parenteral administration by dissolving them in normal saline solution as the vehicle, or in an oil-based vehicle, such as, for example, squalene.

The following examples are provided to illustrate the preparation and activity of the compounds and compositions of the present invention. They are not intended to be limiting upon the scope thereof.

As employed herein, the following abbreviations shall be deemed to have the following meanings:
Boc—tertiary - butoxycarbonyl
But—tertiary - butyl (as ether-forming group)
DCC—N,N'- dicyclohexylurea
DCCI—N,N'- dicyclohexylcarbodiimide
DCM—dichloromethane
DMF—dimethylformamide
DIEA—diisopropylethyl amide
TEA—triethanolamine
TFA—trifluoroacetic acid
HF—hydrogen fluoride
$Me_2S$—dimethyl sulfide
Ala—alanine
Asn—asparagine
Gln—glutamine
Glu—glutamic acid
Gly—glycine
Ile—isoleucine
Leu—leucine
Lys—lysine
Met—methionine
Phe—phenylalanine
Pro—proline
Ser—serine
Thr—threonine
Tyr—tyrosine
Val—valine

EXAMPLE 1

General Procedure for the Solid Phase Synthesis of the Peptide Compounds of the Present Invention Solid phase peptide synthesis (SPPS) is employed according to the method originally described in 1963 by M.B. Merrifield on a Beckman Peptide Synthesizer Model 990B. The method involves coupling amino acids from the carboxy terminal end to the N-terminal end of the peptide once the first amino acid is attached to an insoluble solid support.

The polystyrene resin solid support employed is a copolymer of styrene with about 1% to 2%, by weight, of divinylbenzene as a cross-linking agent which causes the polystyrene polymer to be completely insoluble in most organic solvents, but which causes it to swell extensively in DCM and DMF. This allows the penetration and free transit of solvents and reagents, thus permitting the various chemical reactions to proceed.

The solid support is made functional by the introduction of the insoluble p-methylbenzhydramine. HCl (p-MBHA) resin having free amino groups (0.4 to 0.6 milliequivalents per gram of resin). The resin is swollen by three washes of ten minutes each with DCM with constant stirring. The acidic groups are neutralized with 5% DIEA in DCM to permit attachment of the first amino acid.

The attachment is accomplished by dissolving an excess of Boc-amino acid in 10 milliliters of DCM, or in a mixture of DCM:DMF (2:1), and is activated with 3 equivalents of DCCI in 4 milliliters of DCM. This mixture is employed to couple the first amino acid via its carboxyl group to the activated resin. To assure complete coupling, it is checked by the ninhydrin reaction.

After the first amino acid has been attached, an amino acyl resin had been formed which is used to add the other Boc-amino acids in the desired sequence via a series of steps which results in elongation of the peptide chain.

The steps are as follows:
1. Acid deprotection of the N-terminal group of the attached Boc-amino acid. Selective removal of the Boc group is accomplished with 50% TFA in DCM for 20 minutes.
2. Neutralization of excess acid with 5% DIEA in DCM.
3. Activation and Coupling of the next Boc-amino acid - A Boc-amino acid which was previously activated with DCCI is coupled to the amino acyl resin to form the peptide bond.

The excess of uncoupled amino acid is then removed by filtration and the amount of coupled Boc-amino acid is determined by the ninhydrin reaction. Then the cycle commences once again.

EXAMPLE 2

The general procedure to be followed in each synthesis cycle for each peptide utilizes 4 grams of the dried amino acyl resin, prepared in accordance Example 1 above, and employs the Beckman Peptide Synthesizer Model 990B, wherein the reagents are added stepwise, is as follows:
1. The amino acyl resin is washed four (4) times for 1 minute with 70 mls. of DCM with constant stirring. Excess reagents are removed by suction on the Synthesizer's sintered glass funnel.
2. 70 mls. of a mixture of 40 parts of TFA and 60 parts of DCM are added to the amino acyl resin two (2) times for 1 minute each with constant stirring.
3. 70 mls. of a mixture of 40 parts TFA and 60 parts DCM are added to the amino acyl resin and stirred constantly for 20 minutes.
4. 70 mls. of DCM is added to the amino acyl resin 6 times for 1 minute each with constant stirring.
5. A 70 ml. mixture of 5 parts DIEA and 95 DCM is added twice for 2 minutes with constant stirring.
6. 70 mls. of DCM is added four times for one minute each with constant stirring.
7. Protected amino acid: 3 equivalents in 15 mls. of DCM +DCCI and 3 equivalents in 5 mls of DCM are constantly stirred for 60 minutes.
8. 70 mls. of DCM is added four times for 1 minute each with constant stirring.
9. A 70 ml. mixture of 5 parts DIEA and 95 parts DCM is added while being stirred constantly for 2 minutes.
10. 70 mls. of DCM is added four times for 1 minute each with constant stirring.
11. 70 mls. of DMF is added two times for 2 minutes each with constant stirring.
12. Protected amino acid: 1 equivalent in 5 ml. of DCM at 0° C., add 0.5 equivalents of DCC at 0° C., both for 15 minutes with constant stirring, filter, wash the precipitate for 60 minutes with 15 mls. of DMF with constant stirring.
13. 70 mls. of DMF is added twice with constant stirring for a period of 2 minutes each.
14. 70 mls. of DCM is added four times with constant stirring for 1 minute.
15. Two to five mgs. of sample employed to determine free amino groups by the ninhydrin reaction.

If the result is positive, return to step 9 to perform a third coupling. If negative, a new cycle is begun. The cycles are repeated until the desired sequence is completed. The peptides are obtained by deprotection and cleavage of the obtained product with high and low concentrations of HF.

In the teflon coated reation vessel of the Beckman 990 Synthesizer, there is added 500 milligrams of the synthesized peptide resin and to it is added HF in low concentration, namely, HF/P-Cresol/Me$_2$S (25:10:65, v/v). It is incubated for 2 hours at 0° C. with constant stirring.

By vacuum suction or nitrogen flushing the HF and Me$_2$S is removed and then HF in high concentration is added, namely, HF/P-Cresol (90:10, v/v), incubate for 1 hour at 0° C. with constant stirring. The product is then washed 10 times with 5 mls. of ethyl-ether and the free peptide is extracted with 10 mls. of 5% acetic acid added 10 times.

The crude peptide fraction is analyzed by high performance liquid chromatography in octadesyl (ODS) columns. In most instances the product is free of contaminants, but purification can be achieved, if necessary, by ion-exchange column chromatography or reverse phase liquid chromatography in ODS columns. The amino acid sequence of the peptide is reconfirmed by amino acid sequencing in an automatic Beckman 890M sequencer.

EXAMPLE 3

1 milligram of peptide prepared according to the procedure of Example 2 is coupled to 1 milligram of bovine serum albumin with 20 microliters of glutaraldehyde with constant stirring for 20 hours. The excess of peptide and glutaraldehyde is removed by dialysis against double distilled water overnight.

The coupled peptide is then lyophilized and resuspended in saline solution.

EXAMPLE 4

TABLE 1
POSTCHALLENGE PARASITEMIA IN AOTUS MONKEYS IMMUNIZED WITH SYNTHETIC PEPTIDES
PERCENTAGE OF PARASITEMIA AFTER CHALLENGE ON DAYS

|  | Monkey Number | 4 | 5 | 6 | 7 | 8 | 9 | 10 | 11 | 12 | 13 | 14 | 15 | 16 |
|---|---|---|---|---|---|---|---|---|---|---|---|---|---|---|
| Controls | 358 | .1 | 0 | .9 | .9 | 5.3 | 7.9 | 10.2 | 28.4 | Q | | | | |
|  | 357 | 0 | 0 | .1 | 0 | .5 | 1.6 | 2.8 | 4.0 | 7.4 | 19.0 | Q | | |
|  | 359 | .1 | 0 | .5 | .9 | .9 | 2.4 | 2.5 | 5.4 | 9.0 | 9.0 | 4.5 | 11.5 | 12.0 |
| Mixture | 229 | 0 | 0 | .8 | .5 | 1.5 | 5.0 | 6.6 | 32.5 | Q | | | | |
| of | 255 | 0 | 0 | .6 | 1.0 | 3.7 | 6.7 | 10.9 | 31.0 | | | | | |
| SPf 35.1 | 287 | 0 | 0 | .8 | .8 | 1.0 | 1.6 | 4.1 | 6.0 | 11.8 | 9.6 | 9.8 | 10.0 | 10.5 |
| and | 251 | 0 | 0 | 0 | 0 | 0 | 0 | 0 | .2 | .2 | 1.2 | 3.2 | ND | 11.6 |
| SPf 55.1 | 275 | 0 | 0 | 0 | .1 | .5 | .5 | .5 | 2.0 | 4.0 | 6.5 | 6.0 | 6.6 | ND |
|  | 288 | 0 | 0 | 0 | 0 | .2 | .1 | .0 | 1.0 | .8 | 2.3 | ND | 4.5 | 5.7 |
|  | 289 | 0 | 0 | 0 | .2 | .1 | .2 | 1.0 | 2.3 | 5.4 | 10.4 | 6.8 | 2.7 | 5.4 |
|  | 286 | 0 | 0 | .1 | 0 | .1 | .4 | .4 | 3.5 | 3.7 | 3.2 | ND | .2 | .2 |
| Mixture | 295 | 0 | 0 | 0 | 0 | 0 | 0 | 0 | 0 | 0 | 0 | 0 | 0 | 0 |
| of | 298 | 0 | 0 | 0 | 0 | 0 | 0 | 0 | 0 | 0 | 0 | 0 | 0 | 0 |
| SPf 35.1, | 290 | 0 | 0 | 0 | .1 | 0 | 0 | 0 | .3 | 0 | .7 | .1 | .7 | .4 |
| SPf 55.1 | 291 | 0 | 0 | 0 | 0 | 0 | 0 | 0 | 0 | 0 | 0 | 0 | 0 | 0 |
| and | 297 | 0 | 0 | 0 | 0 | 0 | 0 | 0 | 0 | 0 | 0 | 0 | 0 | 0 |
| SPf 83.1 | 300 | 0 | 0 | 0 | 0 | 0 | 0 | 0 | 0 | 0 | 0 | 0 | 0 | 0 |

|  | Monkey Number | 17 | 18 | 20 | 22 | 24 | 26 | 28 | 30 | 36 | 40 | 45 | 60 | 75 | 90 |
|---|---|---|---|---|---|---|---|---|---|---|---|---|---|---|---|
| Controls | 358 | | | | | | | | | | | | | | |
|  | 357 | | | | | | | | | | | | | | |
|  | 359 | 19.0 | Q | | | | | | | | | | | | |
| Mixture | 229 | | | | | | | | | | | | | | |
| of | 255 | | | | | | | | | | | | | | |
| SPf 35.1 | 287 | Q | | | | | | | | | | | | | |
| and | 251 | Q | | | | | | | | | | | | | |
| SPf 55.1 | 275 | 8.3 | .9 | .6 | .5 | .4 | .1 | 0 | 0 | 0 | 0 | 0 | 0 | 0 | 0 |
|  | 288 | 3.1 | 1.0 | 1.0 | .5 | .1 | 0 | 0 | 0 | 0 | 0 | 0 | 0 | 0 | 0 |
|  | 289 | ND | .2 | .2 | .2 | .1 | 0 | 0 | 0 | 0 | 0 | 0 | 0 | 0 | 0 |
|  | 286 | 0 | .2 | .2 | .2 | .2 | .2 | 0 | 0 | + | | | | | |
| Mixture | 295 | .1 | 0 | .3 | 4.4 | 5.5 | 2.1 | .2 | 0 | 0 | 0 | 0 | 0 | 0 | 0 |
| of | 298 | .3 | 1.3 | 4.8 | .9 | .4 | .1 | 0 | 0 | 0 | 0 | 0 | 0 | 0 | 0 |
| SPf 35.1, | 290 | 2.5 | 1.1 | .6 | 0 | 0 | 0 | 0 | 0 | 0 | 0 | 0 | + | | |
| SPf 55.1 | 291 | 0 | 0 | 0 | 0 | 0 | 0 | 0 | 0 | 0 | 0 | 0 | 0 | 0 | 0 |
| and | 297 | 0 | 0 | 0 | 0 | 0 | 0 | 0 | 0 | 0 | 0 | 0 | 0 | 0 | 0 |
| SPf 83.1 | 300 | 0 | 0 | 0 | 0 | 0 | 0 | 0 | 0 | 0 | 0 | 0 | 0 | 0 | 0 |

Q = beginning of chloroquine therapy designed to save monkey's life
+ = monkey died
ND = Not Determined

IMMUNIZATIONS

Groups of four (4) to six (6) Colombian *Aotus trivirgatus* monkeys were injected on days 0, 30, 45, 60 and 75 with 250 micrograms of each purified and coupled peptide employed in each of the peptide mixtures described hereinafter in Table 1 and the text following thereafter, namely, (a) Formulas I and II, and (b) Formulas I, II and III. Blood samples for antibody studies were taken on days 50, 70 and 80. On day 90, 15 days after the last immunization, the challenge was performed. Each monkey was intravenously inoculated with fresh blood cells infected with $5 \times 10^6$ *P. falciparum* parasites obtained from a donor *Aotus trivirgatus* monkey infected with at least 10% parasitemia of the FVO (Falciparum Vietnam Oak Knoll) strain, adapted to grow in these monkeys in which it induces a lethal disease. The controls, inoculated with saline solution, followed the same immunization pattern.

Parasitemia was monitored daily by peripheral blood smears stained with Giemsa and/or Acridine Orange Flourescence of fresh blood anticoagulated with heparine and diluted 1:1 with saline solution. Partial protection was defined as a significant delay in the appearance of the parasitemia and total protection was defined as less than 10% parasitemia which spontaneously recovered, or a complete absence of parasites in their blood.

In Table 1 the first grouping of three Aotus monkeys represents a control with the monkeys having been inoculated with only normal saline solution. The second grouping in Table 1 represents the data from eight Aotus monkeys immunized with a 1:1, weight-by-weight, mixture of the synthesized peptides of Formulas I and II of the present invention (SPf 35.1 and SPf 55.1). The third grouping in Table 1 represents the data from six Aotus monkeys immunized with a 1:1:1, weight-by-weight, mixture of the synthesized peptides of Formulas I, II and III of the present invention (SPf 35.1, SPf 55.1 and SPf 83.1).

It can be seen from the results in Table 1, that 4 of the 8 Aotus monkeys immunized with the mixture of two synthesized peptides, namely, Formulas I and II, (1:1 w/w), (SPf 35.1 and SPf 55.1) developed a disease similar to the controls, while the remaining 4 developed parasitemias lower than 10% that spontaneously recovered. In these animals, parasitemia continued to be negative until day 90, suggesting a significant protective effect provided by this mixture of two peptides.

In the same challenge, of the 6 monkeys immunized with a mixture of the three peptides, namely, Formulas I, II and III, (1:1:1 w/w), (SPf 35.1, SPf 55.1 and SPf 83.1), three of the six monkeys immunized with this mixture developed a very mild infection with parasitemia maximums of 5%, that peaked 10 to 15 days later than the control group and then spontaneously recovered. The remaining 3 *Aotus trivirgatus* monkeys of this same group, namely, monkeys 291, 297 and 300, did not show any signs of this disease. Furthermore, no parasites at all were detected in blood smear samples up to 90 days after the challenge.

These results show that certain combinations of the peptides synthesized, namely, a mixture of the compounds of Formulas I, II and III, according to the amino acid sequences of these molecules, which had already been shown to offer total or partial immunity against experimental infection, are capable of inducing total, sterile protection in immunized animals.

The development of this immunity is therefore evidence for the use of these mixtures of synthetic peptides in a vaccine against *P. falciparum* induced malaria.

The terms and expressions which have been employed are used as terms of description and not of limitation, and there is no intention in the use of such terms and expressions of excluding any equivalents of the features shown and described or any portions thereof, but it is recognized that various modifications are possible within the scope of the invention as claimed.

What is claimed is:

1. A compound of the formula Tyr-Gly-Gly-Pro-Ala-Asn-Lys-Lys-Asn-Ala-Gly-OH.

2. A compound of the formula Asp-Glu-Leu-Glu-Ala-Glu-Thr-Gln-Asn-Val-Tyr-Ala-Ala-NH$_2$.

3. A compound of the formula Tyr-Ser-Leu-Phe-Gln-Lys-Glu-Lys-Met-Val-Leu-NH$_2$.

4. A compound of the formula Lys-Leu-Tyr-Gln-Ala-Gln-Tyr-Asp-Leu-Ser-Ile-OH.

5. A compound of the formula Lys-Lys-Phe-Thr-Lys-Asp-Glu-Asn-Lys-Pro-Asp-Glu-OH.

6. A composition for vaccinating against *P. falciparum* induced malaria which comprises a mixture of the compounds:

Tyr-Gly-Gly-Pro-Ala-Asn-Lys-Lys-Asn-Ala-Gly-OH     Formula (I)

and

Asp-Glu-Leu-Glu-Ala-Glu-Thr-Gln-Asn-Val-Tyr-Ala-Ala-NH$_2$     Formula (II)

in a vehicle suitable for parenteral administration.

7. The composition according to claim 6 and including in the mixture a peptide compound selected from the group consisting of:

Tyr-Ser-Leu-Phe-Gln-Lys-Glu-Lys-Met-Val-Leu-NH$_2$,     Formula (III)

Lys-Leu-Tyr-Gln-Ala-Gln-Tyr-Asp-Leu-Ser-Ile-OH,     Formula (IV)

or

Lys-Lys-Phe-Thr-Lys-Asp-Glu-Asn-Lys-Pro-Asp-Glu-OH     Formula (V).

8. The composition according to claim 7 wherein the peptide compound is:

Tyr-Ser-Leu-Phe-Gln-Lys-Glu-Lys-Met-Val-Leu-NH$_2$     Formula (III).

9. The composition according to claim 6 wherein the vehicle is normal saline solution.

10. The composition according to claim 6 where in the vehicle is squalene.

11. The composition according to claim 6 wherein the compounds of Formulas I and II are coupled with glutaraldehyde on a weight-to-weight basis to bovine serum albumin.

12. The composition according to claim 6 wherein the compounds of Formula I and II are coupled by copolymerization.

13. The composition according to claim 8 wherein the compounds of Formula I, II and III are coupled with glutaraldehyde on a weight-by-weight basis to bovine serum albumin.

14. The composition according to claim 8 wherein the compounds of Formula I, II and III are coupled by copolymerization.

15. The composition according to claim 8 wherein the weight-by-weight ratio of the compounds of Formula I to Formula II to Formula III is from about 1:1:1 to about 10:10:10.

16. The composition according to claim 15 wherein the weight-by-weight ration is 1:1:1.

17. A method of inducing protective immunity against *P. falciparum* induced malaria which comprises injecting a person with an immunity-inducing effective amount of the composition of claim 8.

18. A method of inducing protective immunity against *P. falciparum* induced malaria which comprises injecting a person with an immunity-inducing effective amount of the composition of claim 13.

19. A method of inducing protective immunity against *P. falciparum* induced malaria which comprises injecting a person with an immunity-inducing effective amount of the composition of claim 14.

* * * * *